United States Patent [19]
Walker et al.

[11] Patent Number: 5,158,528
[45] Date of Patent: Oct. 27, 1992

[54] PERISTALTIC INFUSION DEVICE AND CHARGER UNIT

[75] Inventors: Clarence L. Walker, Webster Groves; Richard A. Sunderland, Creve Coeur; Mark A. Davis, O'Fallon, all of Mo.

[73] Assignee: Sherwood Medical Company, St. Louis, Mo.

[21] Appl. No.: 675,774

[22] Filed: Mar. 27, 1991

Related U.S. Application Data

[63] Continuation-in-part of Ser. No. 538,791, Jun. 15, 1990, Pat. No. 5,057,081.

[51] Int. Cl.$^5$ .............................................. F04E 35/40
[52] U.S. Cl. ................................................... 417/411
[58] Field of Search ................... 417/411, 474, 1, 477

[56] References Cited

U.S. PATENT DOCUMENTS

| | | | |
|---|---|---|---|
| 2,693,765 | 11/1954 | Petri | 103/149 |
| 3,848,592 | 11/1974 | Willock | 128/214 R |
| 3,912,168 | 10/1975 | Mullins et al. | 239/102 |
| 3,927,955 | 12/1975 | Spinosa et al. | 417/477 |
| 3,963,023 | 6/1976 | Hankinson | 128/214 F |
| 4,025,241 | 5/1977 | Clemens | 417/477 |
| 4,138,205 | 2/1979 | Wallach | 417/360 |
| 4,179,249 | 12/1979 | Guttmann | 417/477 |
| 4,184,815 | 1/1979 | Casson et al. | 417/477 |
| 4,187,057 | 2/1980 | Xanthopoulos | 417/63 |
| 4,189,286 | 2/1980 | Murry et al. | 417/477 |
| 4,201,525 | 5/1980 | Brown et al. | 417/477 |
| 4,210,138 | 7/1980 | Jess et al. | 128/214 E |
| 4,217,993 | 8/1980 | Jess et al. | 222/14 |
| 4,230,464 | 12/1980 | Hein | 417/474 |
| 4,231,725 | 11/1980 | Hogan | 417/477 |
| 4,256,442 | 3/1991 | Lamadrid et al. | 417/477 |
| 4,363,609 | 12/1982 | Cosentino et al. | 417/477 |
| 4,460,358 | 7/1984 | Somerville et al. | 604/250 |
| 4,472,116 | 9/1984 | Wenstrup | 417/477 |
| 4,479,797 | 10/1984 | Kobayashi et al. | 604/153 |
| 4,482,347 | 11/1984 | Borsanyi | 604/153 |
| 4,493,706 | 1/1985 | Borsanyi et al. | 604/153 |
| 4,515,535 | 5/1985 | D'Silva | 417/360 |
| 4,540,351 | 9/1985 | Olson | 417/476 |
| 4,552,516 | 11/1985 | Stanley | 417/477 |
| 4,558,996 | 12/1985 | Becker | 417/374 |
| 4,559,040 | 12/1985 | Horres et al. | 604/153 |
| 4,599,055 | 7/1986 | Dykstra | 417/477 |
| 4,653,987 | 3/1987 | Tsuji et al. | 417/360 |
| 4,720,249 | 1/1988 | Krebs et al. | 417/477 |
| 4,758,228 | 7/1988 | Williams | 604/153 |
| 4,813,855 | 3/1989 | Leveen et al. | 417/477 |
| 4,832,584 | 5/1989 | Nassif | 417/477 |
| 4,913,703 | 4/1990 | Pasqualucci et al. | 604/153 |
| 4,925,376 | 5/1990 | Kahler | 417/477 |

FOREIGN PATENT DOCUMENTS

| | | |
|---|---|---|
| 0107440 | 5/1984 | European Pat. Off. . |
| 0173075 | 3/1986 | European Pat. Off. . |
| 57-203891 | 12/1982 | Japan . |
| 2208897 | 4/1989 | United Kingdom . |

OTHER PUBLICATIONS

"Frenta-System for Continuous Tube Feeding", Fresenius AG.

Primary Examiner—Richard A. Bertsch
Assistant Examiner—Alfred Basichas
Attorney, Agent, or Firm—Andrew J. Beck; Montgomery W. Smith; Richard D. Allison

[57] ABSTRACT

A charger unit assembly is disclosed which is particularly adapted to receive a peristaltic pump thereon for charging the batteries of the peristaltic pump and to provide power to the peristaltic pump. A clamp member is mounted on the rear surface of the charger unit to mount the peristaltic pump and charger unit on a support pole. The peristaltic pump includes a rotor member mounted on one side thereof and a swing arm rotatably mounted along the side of the peristaltic pump such that the swing arm is movable between a fluid delivery set loading open position and a closed position which automatically aligns and stretches a portion of the fluid delivery set around the rotor member to ensure that the fluid delivery set is properly aligned about the rotor member of the peristaltic pump.

20 Claims, 8 Drawing Sheets

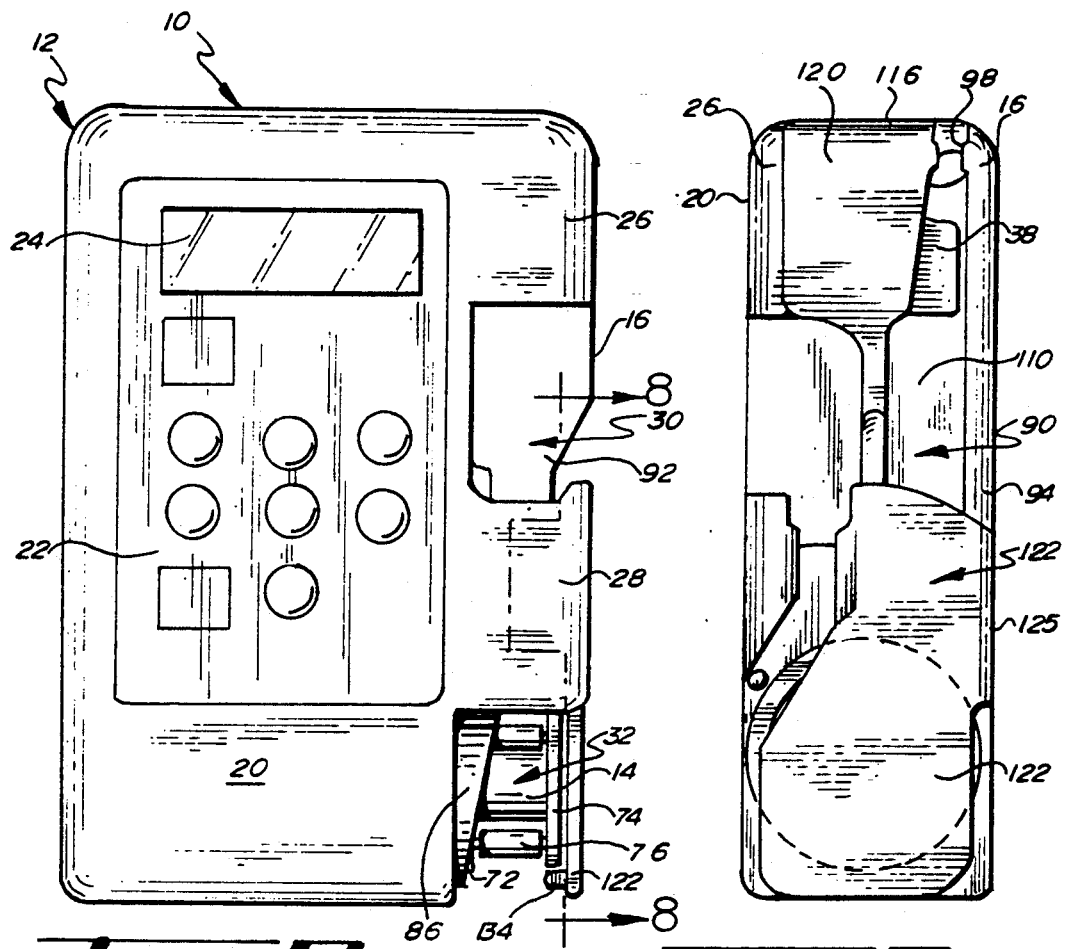
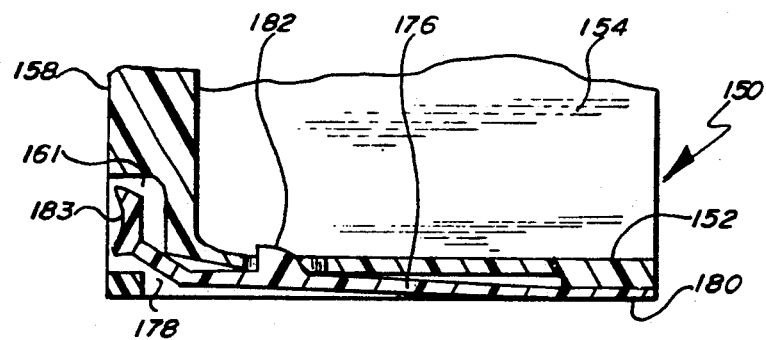

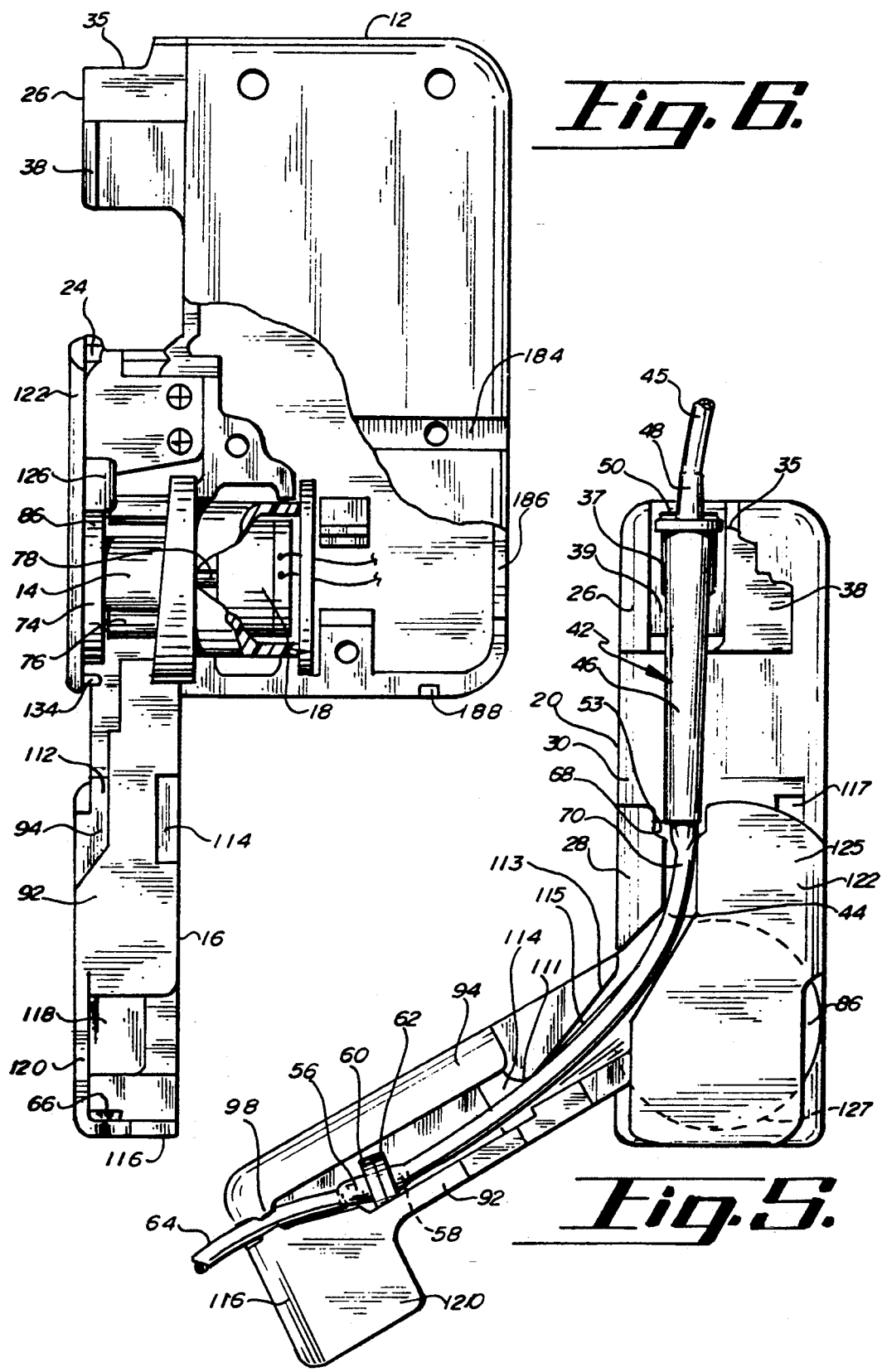

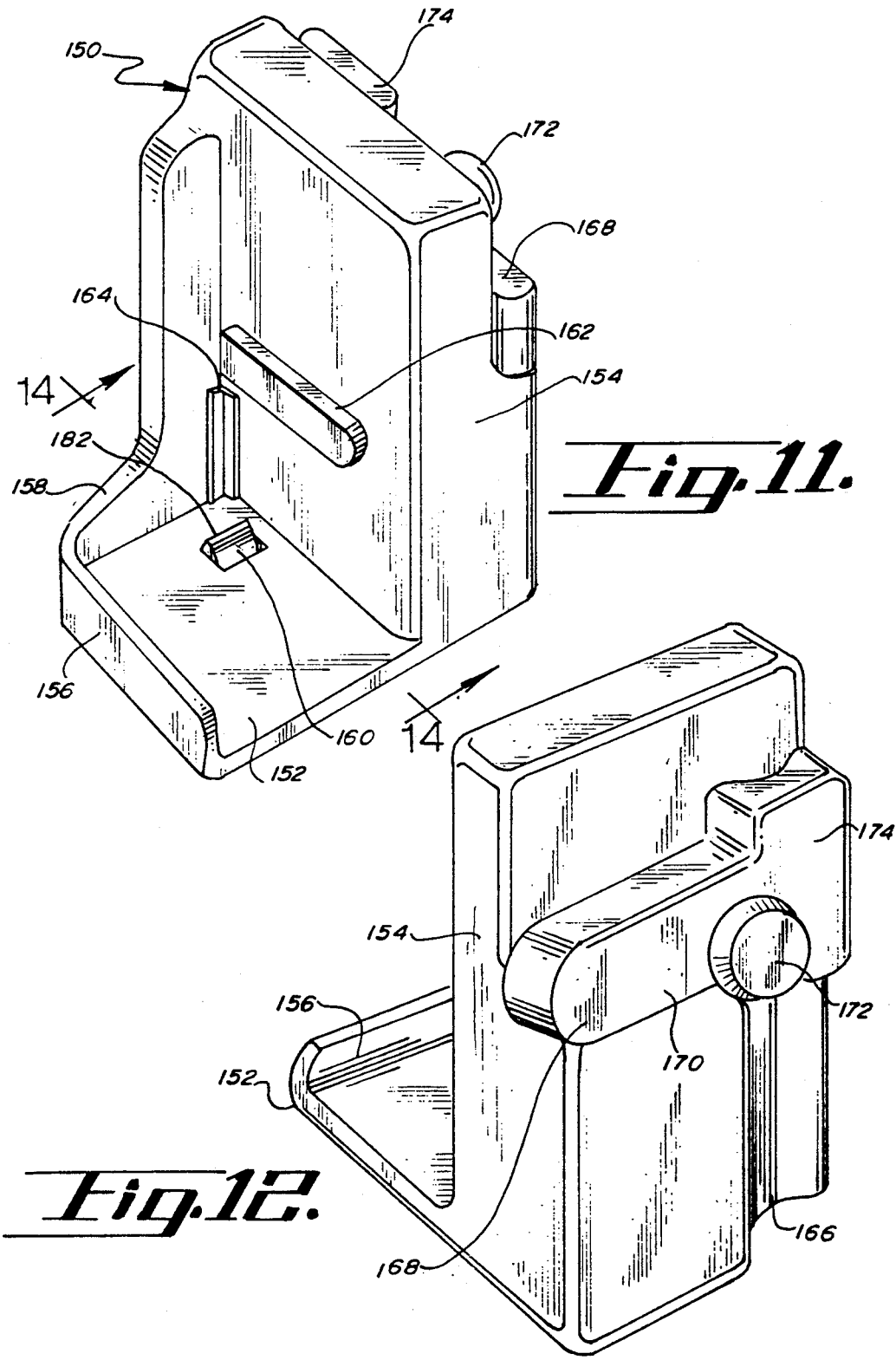

PERISTALTIC INFUSION DEVICE AND CHARGER UNIT

This is a continuation-in-part of copending application Ser. No. 07/538,791 filed on Jun. 15, 1990, now U.S. Pat. No. 5,057,081.

FIELD OF THE INVENTION

The present invention relates to an infusion device for introducing medical fluid into the body of a patient at a controlled rate and more particularly to an infusion device having a swing arm particularly adapted to facilitate the insertion and loading of a resiliently compressible fluid delivery set about the rotor of a peristaltic infusion device.

BACKGROUND OF THE INVENTION

The present invention is adaptable for use on nearly any medical infusion device wherein medical fluids are delivered to the patient through a flexible tubing such that none of the medical fluid comes into direct physical contact with the components of the infusion device. One well known group of infusion devices used in the medical industry are peristaltic pumps. Peristaltic pumps are used in combination with disposable fluid delivery sets or cassettes. Fluid delivery sets generally consist of a cylindrical drip chamber assembly, which is connected to an inlet tube at one end and a resilient and stretchable silicone tube on the other end; a mounting member connected to the second end of the silicone tube and an outlet tube connected between the mounting member and the patient.

Peristaltic pumps are generally classified as being either a rotary peristaltic pump or a linear peristaltic pump. U.S. Pat. No. 4,913,703 granted to Pasqualucci et al discloses a rotary type of peristaltic pump and U.S. Pat. No. 4,493,706 granted to Borsanyi et al discloses a linear type of peristaltic pump, both of which are incorporated herein by reference. Rotary peristaltic pumps commonly include a motor driven rotor mounted on the front surface of the pump. The rotor carries two or more circumferentially spaced apart rollers which are designed to receive the silicone tube of the fluid delivery set mounted thereon. As the motor rotates the rotor, the spaced apart rollers are sequentially brought into contact with the silicone tube to compress portions of the silicone tube. A predetermined volume of medical fluid is contained between the compressed portions of the silicone tube so that a predetermined volume of medical fluid is advanced through the silicone tube as the rotor is rotated by the motor. Because the volume of medical fluid contained between the compressed portions of the silicone tube is a known quantity, the amount of fluid to be delivered to the patient may be regulated by controlling the rate of rotation of the rotor by the motor.

In many of the commonly available rotary peristaltic pumps, the fluid delivery set is mounted in a pair of recesses located on the front surface of the pump such that the drip chamber assembly is received in the first recess and the mounting member is received in the second recess. Once the drip chamber assembly and mounting member have been placed in the respective recesses, the silicone tube must then be stretched to position the silicone tube around the rotor of the peristaltic pump so that portions of the silicone tube are compressed by the rollers on the rotor. When the silicone tube is stretched around the rotor of the peristaltic pump, the silicone tube has a predetermined length and internal diameter.

In an effort to facilitate the mounting of the fluid delivery set on the typical peristaltic pump, the rotor is typically positioned on the front surface of the peristaltic pump so that the entire rotor is exposed. During normal movement of the peristaltic pump from a storage area to a patient's room or during ambulatory use, the peristaltic pump may be accidentally dropped or the rotor of the peristaltic pump may accidentally contact the hospital bed or another object. Although the rotor on the typical peristaltic pump is designed to withstand much of the usual contact which occurs in a hospital, the shaft which connects the rotor to the motor may be damaged. Even though the peristaltic pump may continue to operate, the increased resistance caused by the damaged shaft may dramatically decrease the operating life of the motor or create an inaccurate delivery rate. Because the fluid delivery set is typically changed every day, it is important that the fluid delivery set is manufactured according to fairly rigid manufacturing specifications. The silicone tube of the fluid delivery set is selected so that the internal diameter of the silicone tube will be consistent for each fluid delivery set when the silicone tube is stretched and positioned around the rotor. Oftentimes, the length and diameter of the drip chamber assembly will vary between different manufacturing lots. Because the drip chamber assembly is typically mounted on the peristaltic pump by inserting the bottom end of the drip chamber assembly into a first recess, the top end of the drip chamber assembly may not be properly aligned with the drop sensors on the peristaltic pump. This may result in an incorrect reading of the fluid drops by the drop sensors so that the drop sensors on the peristaltic pump may indicate that there is a flow error and automatically disconnect the motor on the peristaltic pump.

With many of the commercially available peristaltic pumps, the fluid delivery set may be improperly mounted around the rotor if the drip chamber assembly and/or the mounting members are improperly positioned in the respective recesses. With certain peristaltic pump designs, it is also possible for the silicone tube to fall off the rollers of the rotor if the patient accidentally displaces the mounting member or drip chamber assembly from the respective recess during operation of the peristaltic pump. In these situations, it is possible to have an uncontrolled flow of medical fluid to the patient because the rollers of the rotor are not properly compressing the silicone tube to restrict the flow of fluid through the fluid delivery set. If the peristaltic pump is being used to deliver enteral fluid to a patient, the uncontrolled infusion of enteral fluid to the patient may result in aspiration of the fluid into the patient's lungs or over infusion of the enteral fluid.

At present, only one commercially available peristaltic pump includes a safety mechanism to detect the improper mounting of the fluid delivery set on the peristaltic pump. This safety mechanism is disclosed in U.S. Pat. No. 4,913,703 which is assigned to the assignee of the present invention, Sherwood Medical Company. As disclosed in U.S. Pat. No. 4,913,703, the operation of the pump motor is prevented when the fluid delivery set is not detected by the peristaltic pump. Additionally, an alarm will sound if the user attempts to operate the peristaltic pump if the fluid delivery set is not properly mounted on the peristaltic pump.

SUMMARY OF THE INVENTION

It is therefore an object of the present invention to provide an infusion device which is designed to overcome the problems described above and prevent the improper mounting of the fluid delivery set on the infusion device.

It is another object of the present invention to provide an infusion device wherein the fluid delivery set may be quickly and accurately mounted about the rotor of the infusion device.

Another object of the present invention to provide a compact infusion device with a side mounted rotor and swing arm so that the fluid delivery set may be loaded or removed from the infusion device by a nurse or an ambulatory patient.

A further object of the present invention is to provide an infusion device with a swing arm which receives the fluid delivery set in an open position and which properly orients the fluid delivery set around the rotor of the infusion device when the swing arm is moved to the closed position.

A further object of the present invention is to provide a charger unit which is readily mountable on the peristaltic pump to recharge the batteries of the peristaltic pump and/or support the peristaltic pump from a support pole.

One form of the present invention is described hereinafter with particular reference to a rotary peristaltic pump particularly adapted for the infusion of enteral fluids to a patient, however, it should be understood that the present invention may be used on nearly any type of linear or rotary infusion device where it is desirable to ensure that a fluid delivery set is properly mounted on the infusion device to deliver fluid at a controlled rate.

As described more fully hereinafter, the preferred form of the present invention includes a housing assembly having a rotary member extending from one side thereof. The housing assembly further includes a protective covering for the rotary member and a first channel with a plurality of projections and recesses thereon to receive the drip chamber assembly of the fluid delivery set therein. A swing arm on the present invention is operatively mounted on the housing assembly of the peristaltic pump. The swing arm is designed to rotate about the side of the housing assembly between an open first position and a closed second position. In the open position, the swing arm extends downwardly and forwardly from the housing assembly to allow the relaxed fluid delivery set to be readily loaded into the first channel on the housing assembly and a second channel on the swing arm. Once the fluid delivery set is loaded into the housing assembly and swing arm, the swing arm may be rotated to the closed position so that the fluid delivery set is operationally positioned on the peristaltic pump with the silicone tube stretched and properly oriented about the rollers on the rotor of the peristaltic pump.

Once the swing arm is moved to the closed position, the inlet tube on the fluid delivery set extends upwardly from a forward opening at the top of the housing assembly and the outlet tube extends upwardly from a rear opening at the top of the housing assembly. A plurality of openings are formed on the side of the housing assembly to allow the user to visually observe the flow of fluid through the drip chamber assembly and the outlet tube. Additionally, the bottom end of the housing assembly is open to allow the user to observe the operation of the rotor.

A rotor shield is positioned along the side of the housing assembly to protect the rotor and shaft of the present invention from damage caused by accidental contact with an object during movement of the peristaltic pump. Additionally, the present invention includes a drip chamber yoke to align the drip chamber assembly with the optical path of the drop sensors on the housing assembly.

The front surface of the housing assembly includes a control panel and an alpha numeric LED display panel which signals the user when there is a flow error, low battery, system error or when the fluid delivery set is improperly mounted on the peristaltic pump. The motor and electrical circuitry of the present invention are contained within the housing assembly. The rear and bottom surfaces of the housing assembly include a plurality of slots or grooves therein to enable the present invention to be mounted on a charging unit and/or on a support pole when the present invention is used at bedside in a hospital.

An advantage of the present invention is that it is relatively compact and may be used in a hospital setting or with ambulatory patients.

A further advantage of the present invention is that it allows the user to accurately and consistently mount the fluid delivery set about the rotor of the present invention.

A further advantage of the present invention is that it allows the user to visually observe the flow of fluid through the fluid delivery set.

A further advantage of the present invention is that the rotor is protected by a rotor shield which is mounted on the housing assembly.

A further advantage of the present invention is that the relatively compact peristaltic pump is readily mountable on an aesthetically attractive charger unit.

Further objects and advantages of the present invention are described hereinafter and will become apparent by reviewing the drawings and detailed description of the preferred embodiment as set forth herein.

BRIEF DESCRIPTION OF THE DRAWINGS

FIG. 2 is a frontal elevational view of the assembled peristaltic pump in accordance with the present invention having the swing arm in the closed position;

FIG. 3 is a side elevational view of the peristaltic pump in accordance with the present invention having the swing arm in the closed position;

FIG. 5 is a side elevational view of the peristaltic pump as shown in FIG. 4 and including a fluid delivery set loaded operationally mounted on the peristaltic pump in accordance with the present invention;

FIG. 6 is a rear elevational view, partially in cross section, of the peristaltic pump in accordance with the present invention having the swing arm in the open position and showing the motor and rotor shaft of the present invention;

FIG. 11 is a frontal elevational view of the charger unit of the present invention;

FIG. 12 is a rear elevational view of the charger unit of the present invention;

FIG. 14 is a cross-sectional view of the charger unit taken along lines 14—14 of FIG. 11 showing the latch member of the present invention;

DETAILED DESCRIPTION OF THE PREFERRED EMBODIMENT

As shown in FIGS. 1-10, the preferred form of the present invention includes a rotary type of peristaltic pump 10 particularly adapted for the controlled delivery of enteral fluid to a patient. It should be understood that although the present invention is described herein with reference to a rotary type of peristaltic pump, the present invention is readily adaptable for use with nearly any type of rotary or linear pump wherein it is desired to deliver a fluid at a controlled rate through a tubular member that is mounted along at least a portion of the pump.

Figure 1:
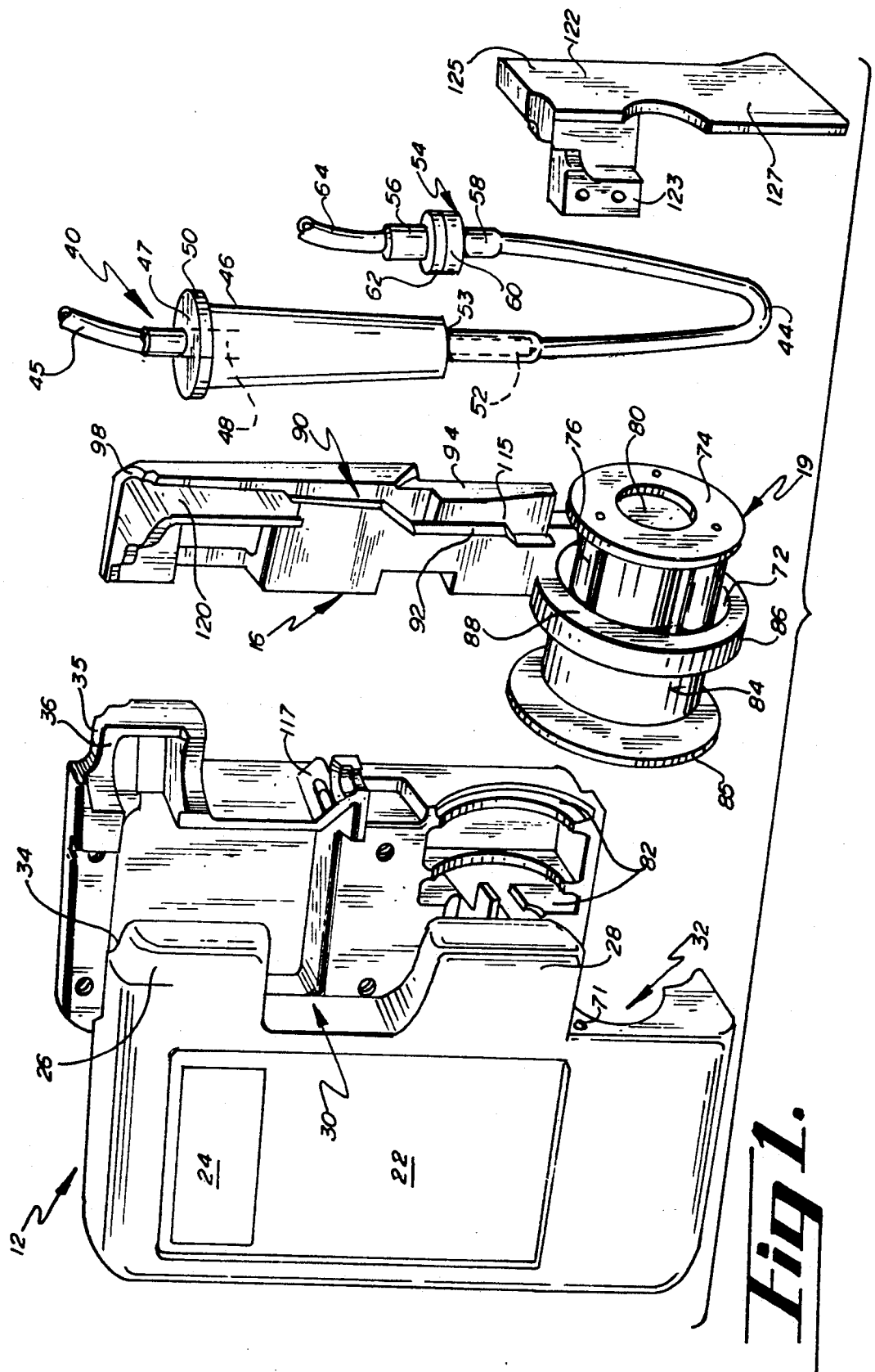
FIG. 1 is an exploded perspective elevational view of the housing assembly; swing arm; rotor; fluid delivery set and rotor shield; of the present invention with the drip chamber yoke removed.

The peristaltic pump 10 of the present invention consists generally of a rectangularly-shaped housing assembly 12 having a swing arm 16 pivotally mounted on the lower side surface thereof. The swing arm 16 includes carrying a motor 18 and partially enclosed rotor 14 mounted thereon as described hereinafter. As shown in FIGS. 1 and 2, the front surface 20 of the housing assembly 12 is a generally flat and rectangularly-shaped surface which includes a control panel section 22 and an alpha numeric LED display section 24. The right side of the front surface 20 includes an outwardly extending elongate upper flange 26 which extends downwardly from the top portion of the front surface 20 along approximately one-fourth of the length of the housing assembly 12 to shield the top portion of the drip chamber assembly 42, as described more fully hereinafter. An elongate lower flange 28 extends outwardly along approximately one-fourth of the length of the housing assembly 12 near the approximate mid section of the housing assembly 12 to position the lower section of the drip chamber assembly 42 and a first portion of the silicone tube 44 of the fluid delivery set 40 as described more fully hereinafter. A first opening 30 is located between the upper flange 26 and the lower flange 28 to allow the user to observe the flow of fluid in the drip chamber assembly 42 during operation of the peristaltic pump 10. A second opening 32 is located beneath the lower flange 28 on the right side of the housing assembly 12 to allow the user to observe the operation of the rotor 14 of the present invention.

As described briefly above, the peristaltic pump 10 of the preferred embodiment is particularly designed for use with a conventional fluid delivery set 40 as disclosed in U.S. Pat. No. 4,913,703, which is incorporated herein by reference. The conventional fluid delivery set 40 allows medical fluid to flow therethrough and generally consists of an elongate and flexible inlet tube 45 which is connected to a source of fluid (not shown) at one end and the top of the drip chamber assembly 42 at the other end. The drip chamber assembly 42 preferably consists of a semi-rigid and cylindrically-shaped tapered member 46 having a top cap member 47 attached to the top end thereof. An annular rim 50 is formed as part of the cap member 47 and is located along the top surface of the tapered member 46. a top tubular member 48 extends downwardly from the cap member 47 into the interior of the drip chamber assembly 42. A lower tubular member 52 is centrally positioned on the bottom end 53 of the tapered member 46 to extend downwardly therefrom. The lower tubular member 52 on the drip chamber assembly 42 is connected to the first end of the silicone tube 44. The silicone tube 44 preferably consists of a predetermined length of resilient and compressible silicone tubing having a first predetermined internal diameter in the relaxed condition and a second predetermined internal diameter in the stretched condition as described hereinafter. The second end of the silicone tube 44 is connected to a circular mounting or connector member 54 which includes top and bottom tubular members, 56 and 58 respectively, which extend upwardly and downwardly therefrom and an enlarged annular flange 60 which is positioned between the top and bottom tubular members, 56 and 58, In the preferred form of the present invention, the annular flange 60 includes a cylindrically-shaped magnet 62 thereon, the function of which is described more fully hereinafter. The magnet 62 may be obtained from a variety of sources; however, it has been found that a material composed of 88% strontium ferrite is particularly suitable for use in the present invention. This material includes 12% of #6 nylon and is available from Tengam Inc. of Otsego, Mich. The magnet 62 is magnetized in the axial direction to a magnetic strength of approximately 400 to 500 gauss at the circumferential surface. An elongate outlet tube 64 includes a first end which is connected to the top tubular member 56 of the mounting member 54 and a second end (not shown) which is adapted to deliver the medical fluid to the patient.

Figure 4:
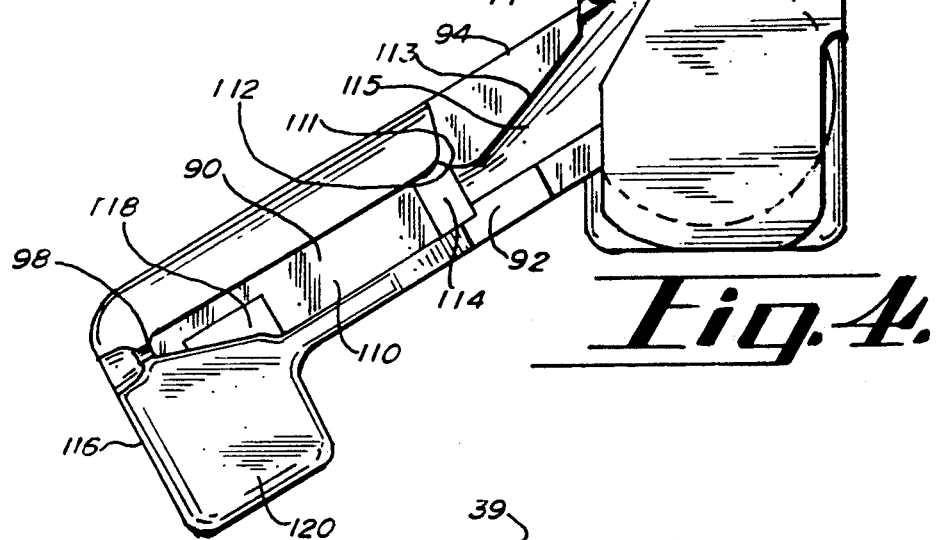
FIG. 4 is a side elevational view of the peristaltic pump in accordance with the present invention having the swing arm in the open position.

As best shown in FIGS. 4-6, the upper flange 26 on the side surface of the housing assembly includes a semi-circularly-shaped top lip 34 which extends rearwardly and inwardly from the top of the upper flange 26. The top lip 34 is shaped to protect the inlet tube 45 near the top tubular member 48 of the drip chamber assembly 42 and assist in the loading of the drip chamber assembly 42 onto the peristaltic pump 10 when the fluid delivery set 40 is mounted on the peristaltic pump 10 as described hereinafter. The upper flange 26 includes an elongate and semi-circular drip chamber yoke retaining flange 36 which consists of a set of flanges and recesses which are located rearwardly of the front surface 20 of the upper flange 26 to retain the drip chamber yoke 37 in fluid tight communication with the housing assembly 12 to allow the user to clean the drip chamber recess 39 without exposing the electronics in the housing assembly 12 to the cleaning fluid. The retaining flange 36 is positioned on the upper flange 26 to locate the drip chamber yoke 37 adjacent to the drop forming bottom end of the top tubular member 48 on the drip chamber assembly 42 as described hereinafter. A generally rectangularly-shaped tube retaining flange 38 extends rearwardly from the outer surface of the yoke retaining flange 36. The tube retaining flange 38 is oriented in a spaced apart relationship with the housing assembly 12 to retain a portion of the outlet tube 64 from the fluid delivery set 40 adjacent thereto when the swing arm 16 is in the closed position as described hereinafter. A locking lip 35 is positioned rearwardly of the yoke retaining flange 36 and is oriented to extend perpendicular to and upwardly from the tube retaining flange 38. The locking lip 35 is adapted to receive a complementary locking lip 66 on the swing arm 16 therein. The locking lip 35 on the housing assembly 12 and the locking lip 66 on the swing arm 16 may be replaced by nearly any type of positive latch including the type of latch mechanism having one or more magnets thereon to ensure retention of the swing arm 16 in the closed position as described hereinafter.

Figure 10:
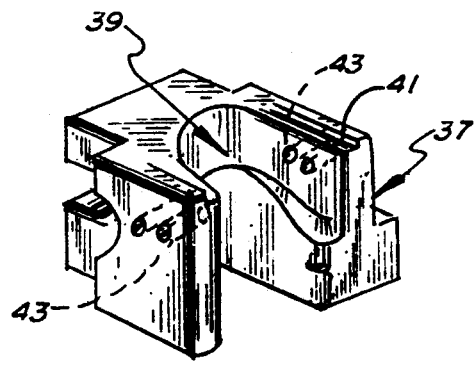
FIG. 10 is an enlarged and elevated perspective view of the drip chamber yoke of the present invention as shown in FIG. 4.

As shown in FIGS. 4 and 10, the drip chamber yoke 37 of the present invention is a rigid and generally rectangularly-shaped member having a drip chamber receiving recess 39 along the interior surface thereof. The top of the receiving recess 39 includes an enlarged and generally oblong shoulder area 41 which is adapted to receive the relatively rigid annular rim 50 of the drip chamber assembly 42 thereon as described hereinafter. The internal surface of the receiving recess 39 below the shoulder area 41 is semi-circularly-shaped with a radius of approximately 240° to retain the drip chamber assembly 42 centered therein and to decrease the likelihood that the drip chamber assembly 42 will be inadvertently pulled from the optimal vertical alignment in the receiving recess 39 during operation of the present invention. The lengthwise dimension of the receiving recess 39 forms an angular recess which gradually tapers inwardly to conform to the shape of the tapered member 46 of the drip chamber 42. As shown in FIG. 10, two opposingly oriented pairs of openings 43 are located in the side walls of the drip chamber yoke 37. The openings 43 are designed to house at least one set of drop sensing emitters and detectors (not shown). The drop sensing emitters and detectors are aligned to form an optical path which detects drops of fluid immediately after they fall from the bottom end of the top tubular member 48 in the drip chamber assembly 42.

If the emitters and detectors are positioned too high with respect to the bottom end of the top tubular member 48, The optical path may be aligned with the bottom end of the top tubular member 48. In this situation, the peristaltic pump 10 may not detect the formation of drops in the drip chamber assembly 42 and the motor 18 of the peristaltic pump 10 will stop operating and indicate to the operator that there is a flow error. If the emitters and detectors are positioned too low with respect to the bottom end of the top tubular member 48, the peristaltic pump 10 may not detect the drops of medical fluid because the lower portion of the tapered member 46 may become coated with enteral fluid due to the splashing of the drops as they fall in the drip chamber assembly 42. In this situation, the peristaltic pump 10 will then stop operating and indicate to the user that there is a flow error because the fluid drops are not being sensed by the emitters and detectors.

Finally, if the emitters and detectors are not optimally positioned with respect to the bottom end of the top tubular member 48, the user may also experience a flow error alarm if the peristaltic pump 10 is tilted so that the drops in the drip chamber assembly 42 do not fall through the optical path of the emitters and detectors. If the emitters and detectors are positioned too far below the bottom end of the top tubular member 48 and the peristaltic pump 10 is not maintained in a vertical position, the falling drops of medical fluid may not pass through the optical path of the emitters and detectors and the peristaltic pump 10 will discontinue operating and indicate to the user that there is a flow error. When the present invention is used as an ambulatory infusion device, it is much more likely that the peristaltic pump 10 will be operated in a position which is not completely vertical and therefore the incidence of flow error alarms due to the failure of the emitters and detectors to detect the falling drops will likewise increase. Therefore, as described hereinafter, the drip chamber yoke 37 of the present invention is designed to ensure that the bottom end of the top tubular member 48 is optimally positioned adjacent to the optical path created by the emitters and detectors.

As discussed briefly above, the length of the drip chamber assembly 42 may also vary between individual fluid delivery sets 40. In prior peristaltic pumps, the drip chamber assembly is retained in position on the peristaltic pump by inserting the bottom end of the drip chamber assembly into a first recess on the housing assembly and there is nothing to ensure that the bottom end of the top tubular member in the drip chamber assembly 42 is optimally positioned so that the drop will pass through the optical path. Because the fluid delivery set 40 is changed everyday, the present invention is designed to accommodate variations in the length of drip chamber assemblies 42 without adversely affecting the drop sensing operation of the peristaltic pump 10 by ensuring that the emitters and detectors are optimally positioned with respect to the bottom end of the top tubular member 48 while not adversely affecting the distance the silicone tube 44 is stretched about the rotor 14. The drip chamber assembly 42 of the preferred fluid delivery set 40 has a nominal length of 2.5075 inches and cumulative dimensional tolerance of ±0.035 inches. The drip chamber yoke 37 of the present invention allows the bottom end 53 of fluid delivery sets 40 which have a longer drip chamber assembly 42 to rest on the first mounting recess 68 so that a minimal amount of the top end of the drip chamber assembly 42 will extend above the shoulder area 41 of the drip chamber yoke 37 and the optical path of the emitters and detectors will be only slightly below the optimal position with respect to the bottom end of the top tubular member 48. The fluid delivery sets 40 which have a shorter drip chamber assembly 42 will be supported in the drip chamber yoke 37 by contact between the annular rim 50 of the drip chamber assembly 42 in the shoulder area 41 of the receiving recess 39 so that the bottom end of the top tubular member 48 will be optimally positioned with respect to the optical path of the emitters and detectors. When the shorter drip chamber assembly 42 is supported by the shoulder area 41 in the drip chamber yoke 37, the silicone tube 44 may be stretched slightly more than when the bottom end 53 of the drip chamber assembly 42 is supported in the first mounting recess 68; however, because the stretching of the silicone tube 44 is distributed over the entire length of the silicone tube 44, the internal diameter of the silicone tube 44 is not significantly affected and the amount of enteral fluid delivered by each rotation of the rotor 14 on the peristaltic pump 10 is not adversely affected.

As shown in FIG. 4, an oblong and generally semi-circular first mounting recess 68 is positioned behind the front surface of the lower flange 28 and slightly below the top surface thereof. The first mounting recess 68 includes a grooved shoulder area 69 which is sized to receive the bottom end 53 of the drip chamber assembly 42 therein while allowing the lower tubular member 52 of the drip chamber assembly 42 to extend therethrough. A first set loading channel 70 extends downwardly from the first mounting recess 68 to the top end of the second opening 32 which begins slightly below the top of the rotor 14. A raised frictional detent 71 is located beneath the lower flange 28 near the front surface of the housing assembly 12 to releasably retain the swing arm 12 in the open position as described hereinafter.

As shown in FIG. 1, the rotor 14 of the present invention is a cylindrical member having inner and outer enlarged flanges 72 and 74, respectively. As described above, the rotor is designed to extend from the side surface of the housing assembly 12. The enlarged flanges, 72 and 74, include three equally spaced rollers 76 extending therebetween along the circumference of the rotor 14. The rollers 76 are mounted on metal pins which extend between the inner and outer enlarged flanges 72 and 74 so that the rollers 76 rotate freely when they are placed in contact with the silicone tube 44 of the fluid delivery set 40 as described hereinafter. The rotor 14 is mounted on an inwardly directed central shaft 78 (FIG. 6) which extends from the inner enlarged flange 72 to the motor 18 so that the rotational forces created by the motor 18 are transferred directly to the rotor 14. A circular recess 80 is located on the central axis of the rotor 14 along the outer surface of the outer enlarged flange 74, the function of which is described hereinafter.

The interior of the housing assembly 12 includes the electronic circuitry (not shown) of the peristaltic pump 10 and a pair of annular grooves 82 located inwardly from the rotor 14 as shown in FIG. 1. The swing arm 16 of the present invention includes a hollow and cylindrically-shaped bearing sleeve 84 which extends inwardly from the side surface of the housing assembly 12. The motor 18 of the present invention is frictionally retained in the bearing sleeve 84 so that the motor 18 rotates as the swing arm 16 is rotated between the open and closed positions. The external surface of the bearing sleeve 84 includes a pair of inner and outer circular flanges 85 and 86, respectively, which are received in the annular grooves 82 on the housing assembly 12 to allow rotational movement of the swing arm 16 while preventing longitudinal movement of the swing arm 16 and motor 18 with respect to the housing assembly 12. The outer circular flange 86 includes an outwardly directed lip 88 which encircles the circumference of the inner flange 72 on the rotor 14. The bottom of the lip 88 is positioned slightly inwardly from the outer surface of the inner flange 72 and increases in outward extension from the bottom of the rotor 14 to the top of the rotor 14 wherein the lip 88 extends outwardly from the outer surface of the inner flange 72 to assist in the placement of the silicone tube 44 around the rotor 14 as described hereinafter.

Figure 9:
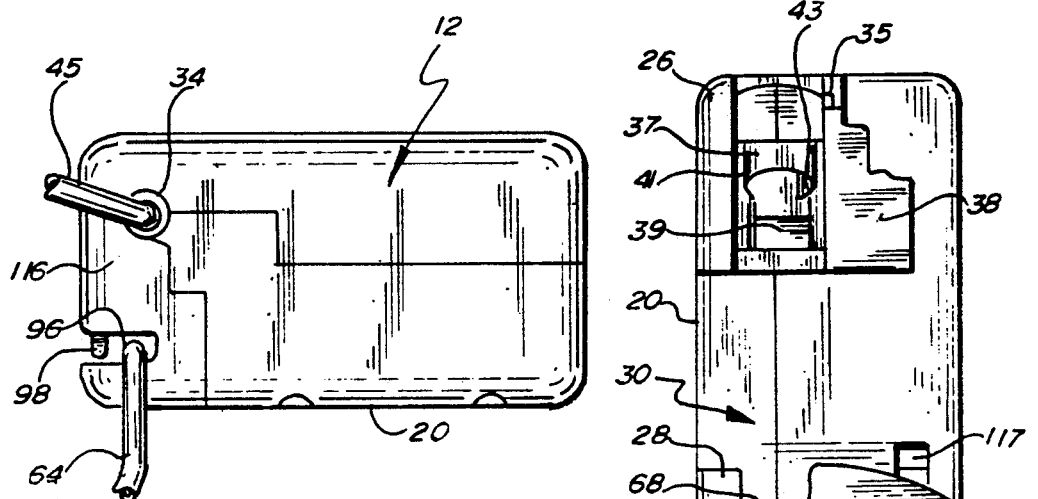
FIG. 9 is a top elevational view of the peristaltic pump in accordance with the present invention with a fluid delivery set inserted therein and having the swing arm in the closed position.
Figure 7:
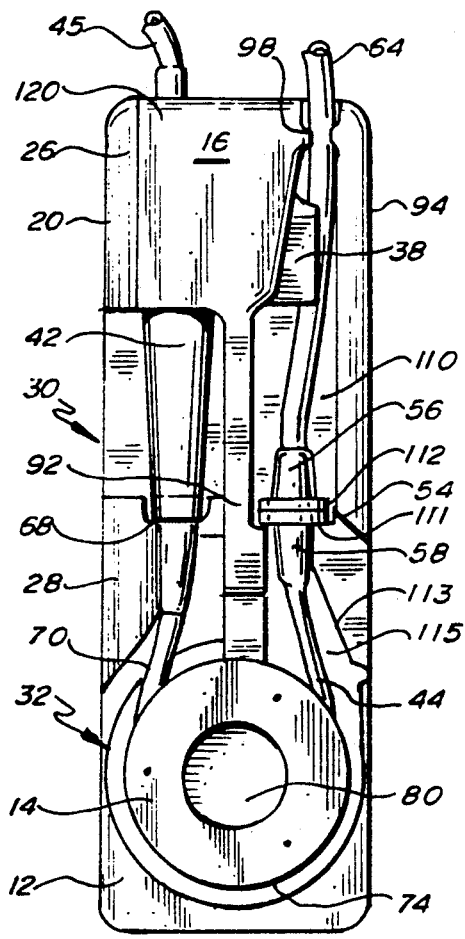
FIG. 7 is a side elevational view of the peristaltic pump in accordance with the present invention, as shown in FIG. 3, with the rotor shield removed; a fluid delivery set inserted in the peristaltic pump and the swing arm in the closed position.

As shown in FIG. 4, a second set loading channel 90 is formed along the lengthwise dimension of the swing arm 16 by first and second wall members, 92 and 94 which extend outwardly from the inner surface of the swing arm 16. As shown in FIGS. 5, 7 and 9, the second set loading channel 90 is generally U-shaped and includes a top semi-circular opening 96 through which the outlet tube 64 of the fluid delivery set 40 extends. A pair of inwardly directed ridges 98 are positioned slightly below the top surface 116 of the swing arm 16. The ridges 98 extend inwardly approximately two thirds of the way into the second set loading channel 90 so that the exterior portion of this area of the second set loading channel 90 is narrower than the interior portion of this section of the loading channel 90. The width of the exterior surface of the second set loading channel 90 gradually increases from the ridges 98 near the top surface 116 of the swing arm 16 to a location approximately one-fourth of the distance along the swing arm 16 to a lower enlarged width area defined herein as the mounting member receiving section 110 of the second set loading channel 90. The receiving section 110 of the second set loading channel 90 is an elongate and generally rectangularly-shaped recess in the swing arm 16. The receiving section 110 is sized to conveniently receive the mounting member 54 and the second end of the silicone tube 44 of the fluid delivery set 40 therein. The bottom end of the receiving section 110 is aligned with a lower silicone tube channel 115 which forms the lower section of the second set loading channel 90. The top end of the silicone tube channel 115 includes a semi-circular and reduced width second mounting recess 112 which forms a shoulder area 111 in the second set loading channel 90. The shoulder area 111 is adapted to receive the bottom of the mounting member 54 thereon as described hereinafter. The silicone tube channel 115 includes a gradually tapered section 113 on the second wall member 94 which tapers rearwardly and downwardly along the swing arm 16 to increase the width of the second set loading channel 90 from a location below the second mounting recess 112 to the bottom of the second wall member 94. The second wall member 94 is designed to end below the top of the rotor 14 while the first wall member 92 extends generally linearly downwardly from the second mounting recess 112 to a location adjacent the top of the rotor 14 when the swing arm 16 is in the closed position as described hereinafter.

As shown in FIG. 4, the inner surface of the second set loading channel 90 includes a sensor opening 114 located immediately above and adjacent to the second mounting recess 112 to allow a magnetic sensor 117 to sense when the mounting member 54 is inserted in the swing arm 16 and the swing arm 16 is moved to the closed position as described hereinafter. The magnetic sensor 117 of the present invention is preferably a magneto resistive switching element, such as part No. SS21PE available from Microswitch Inc. of Freeport, Ill. which is designed to provide an output of plus 5 volts when not in the presence of a magnetic field and zero volts when in the presence of either polarity of a magnetic field such as the magnetic field created by magnet 62. The inner surface of the swing arm 16 also includes second opening 118 located below the top surface 116 of the swing arm 16 and above the receiving section 110 of the second set loading channel 90. The second opening 118 is sized to receive the retaining flange 38 of the housing assembly 12 therethrough when the swing arm 16 is in the closed position. As shown in FIG. 6, the top surface 116 of the swing arm 16 includes a locking lip 66 extending downwardly and linearly along the inner surface of the top surface 116 so that the locking lip 66 contacts the locking lip 39 on the housing assembly 12 to releasably retain swing arm 16 in the closed position. The top of the swing arm 16 also includes a flat and generally rectangularly shaped drip chamber shade 120 (FIGS. 4 and 5) which is designed to protect the emitters and detectors in the drip chamber yoke 37 and the top of the drip chamber assembly 42 from interference by ambient light when the swing arm 16 is in the closed position as described hereinafter.

Figure 8:
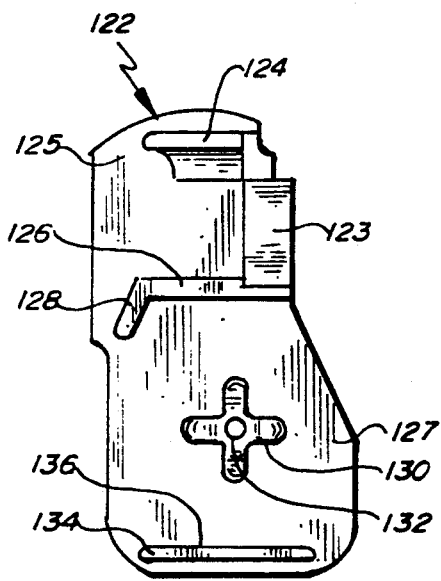
FIG. 8 is an enlarged and elevational side view of the rotor shield taken generally along line 8—8 of FIG. 2.

As shown in FIGS. 1 and 8, the preferred embodiment of the present invention includes a rotor shield 122 to facilitate the loading of the fluid delivery set 40 around the rotor 14 and to protect the rotor 14 and shaft 78 from accidental damage caused by contact with the rotor 14 during movement of the peristaltic pump 10. The rotor shield 122 includes a mounting surface 123 which is attachable to the side surface of the housing assembly 12 at a location on the housing assembly 12 which is oriented rearwardly from the lower flange 28. The rotor shield 122 is designed to be removable from the housing assembly 12 so that the rotor 14 and rotor shield 122 may be cleaned without exposing the electronics in the housing assembly 12 to the cleaning fluid. The mounting surface 123 extends outwardly therefrom to a generally planar portion of the rotor shield 122 which is generally aligned with the outer surface of the swing arm 16. The planar surface of the rotor shield 122 consists generally of a flat and rectangularly-shaped upper section 125 and an oblong-shaped lower section 127. The upper section 125 and the lower section 127 of the rotor shield 122 are positioned along the side surface of the housing assembly 12 to extend downwardly from the lower flange 28 and along the side surface of the housing assembly 12 to a location spaced outwardly from the outer flange 74 of the rotor 14. As shown in FIG. 8, the inner surface of the rotor shield 122 near the top of the upper section 125 includes an inwardly directed and generally linear top flange 124 which extends inwardly from the rotor shield 122 to a location adjacent to the top of the second mounting recess 112 on the swing arm 16 when the swing arm 16 is in the closed position. The top flange 124 and the second mounting recess 112 form a generally closed recess having a closed section only slightly larger than the diameter of the mounting member 54. The top of the top flange 124 also includes a chamfer thereon to facilitate the movement of the mounting member 54 into the second mounting recess 112 as the swing arm 16 is moved to the closed position as described hereinafter. An elongate and generally L-shaped intermediate flange 126 extends inwardly from the approximate intersection of the upper section 125 and lower section 127 of the rotor shield 122. The intermediate flange 126 extends inwardly from the rotor shield 122 to a location which is adjacent to the top of the rotor 14 and extends inwardly of the outer flange 74 of the rotor 14. The rear end 128 of the intermediate flange 126 is oriented at an angle of approximately 65° from the main portion thereof and extends downwardly therefrom to a location adjacent to the tapered section 113 on the second wall member 94 of the swing arm 16 when the swing arm 16 is in the closed position.

As shown in FIG. 8, a centrally positioned set of stiffening ribs 130 extend inwardly from the center of the lower section 127 of the rotor shield 122. The ribs 130 preferably include four laterally extending arms which are designed to be normally spaced apart from the circular recess 80 located on the outer flange 74 of the rotor 14. The ribs 130 are designed to reduce the bending forces applies to the lower section 127 of the rotor shield 122 when an external force is applied to the rotor shield 122. Additionally, a circular protrusion 132 extends inwardly from the center of the ribs 130. The orientation of the ribs 130 with respect to the circular recess 80 decreases the likelihood that the shaft 78 of the rotor 14 will be bent or damaged by contact between the side of the peristaltic pump 10 or rotor 14 and an external object. The circular protrusion 132 is aligned with the axial center of the rotor 14 and allows the rotor 14 to continue rotating with only a slight increase in resistance to rotation when the side of the peristaltic pump 10 rests against an object. Therefore, the operation of the motor 14 of the present invention will not be significantly affected by moderate contact with an external object against the side of the peristaltic pump 10 of the type which may occur during ambulatory use. The bottom edge of the rotor shield 122 includes an inwardly directed bottom flange 134 which has an apex 136 thereon located approximately midway along the lengthwise dimension of the bottom flange 134. The apex 136 preferably extends inwardly from the rotor shield 132 to a location adjacent to the inner surface of the outer flange 74 on the rotor 14 and is designed to guide the fluid delivery set 40 toward the center of the rollers 76 on the rotor 14 on those occasions when the fluid delivery set 40 is not loaded completely flat in the first and second set loading channels 70 and 90, as described hereinafter.

The installation of the fluid delivery set 40 on the peristaltic pump 10 of the present invention is relatively simple and the likelihood that the fluid delivery set 40 will be improperly mounted on the peristaltic pump 10 is significantly reduced as compared to currently available peristaltic pumps. Initially, the swing arm 16 is rotated to the open or loading position so that the inner surface of the swing arm 16 contacts the frictional detent 71 as shown in FIG. 4. In this open position, the drip chamber receiving recess 39; the first mounting recess 68; the first set loading channel 70 on the housing assembly 12 and the entire second set loading channel 90 on the swing arm 16 are exposed to allow for the insertion of the fluid delivery set 40 therein. Initially, the drip chamber assembly 42 of the fluid delivery set 40 is placed on the housing assembly 12 by inserting the annular rim 50 of the drip chamber assembly 42 below the top lip 34 of the housing assembly 12 so that the bottom end 53 of the drip chamber assembly 42 is positioned above the first mounting recess 68. The mounting member 54 is then inserted into the receiving section 110 of the second set loading channel 90 on the swing arm 16 such that the silicone tube 44 is loosely positioned near the front surface of the rotor 14. Finally, the outlet tube 64 is pulled inwardly between the ridges 98 into the wider interior of the second set loading channel 90 on the swing arm 16. The width of the silicone tube channel 115 and the semi-circular opening 96 are sized so that the mounting member 54 will only fit in the receiving section 110 of the second set loading channel 90. Additionally, the second set loading channel 90 on the swing arm 16 is sized so that it will not accept the drip chamber assembly 42 therein and therefore, the user cannot accidentally reverse the drip chamber assembly 42 and mounting member 54 while loading the fluid delivery set 40 on the present invention.

The swing arm 16 of the present invention is particularly designed so that the swing arm 16 rotates generally about the axial center of the rotor 14 from the open position (FIGS. 4, 5 and 6) to the closed position (FIGS. 2, 3 and 7). The orientation of the swing arm 16 about the axial center of the rotor increases the relative distance between the first mounting recess 68 on the housing assembly 12 and the second mounting recess 112 on the swing arm 16 through the first set loading channel 70 and the silicone tube channel 115 as the swing arm 16 is moved from the open position to the closed position. Once the fluid delivery set 40 has been inserted in the housing assembly 12 and swing arm 16 as described above, the silicone tube 44 of the fluid delivery set 40 will remain in the relaxed and unstretched condition near the front of the rotor 14 until the swing arm 16 is rotated to a position generally perpendicular to the rear surface of the peristaltic pump 10. As the swing arm 16 reaches this position, the silicone tube 44 will contact the rollers 76 on the rotor 14. As described above, if the silicone tube 44 is not initially aligned near the rollers 76 on the rotor 14, the silicone tube 44 will contact the bottom flange 134 on the rotor shield 122 and slide inwardly as the swing arm 16 is rotated so that the silicone tube 44 is properly positioned about the rollers 76 on the rotor 14. Continued rotation of the swing arm 16 will cause the mounting member 54 to be drawn downwardly in the receiving section 110 of the loading channel 90 until the bottom surface of the mounting member 54 is positioned inwardly of the top flange 134 on the rotor shield 122 to contact the shoulder area 111 in the top of the second mounting recess 112. Additionally, as described above, the drip chamber assembly 42 will be pulled downwardly in the drip chamber receiving recess 39 until the annular rim 50 of the drip chamber assembly 42 contacts the shoulder area 41 in the drip chamber yoke 37 or until the bottom end 53 of the tapered member 46 contacts the shoulder area 69 in the top of the first mounting recess 68. Continued rotation of the swing arm 16 causes the silicone tube 44 to be stretched and compressed around the rollers 76 on the rotor 14. When the swing arm 16 is rotated to the closed position as shown in FIGS. 2 and 3, the locking lip 66 on the swing arm 16 will contact the locking lip 35 on the housing assembly 12 so that the swing arm 16 will be frictionally retained in the closed position.

When the swing arm 16 is in the closed position as shown in FIG. 7, the inlet tube 45 extends through an opening in the top surface of the housing assembly 12 formed by adjacent semi-circular edges of the swing arm 16 and the top lip 34 of the upper flange 26 (FIG. 9). The bottom end of the top tubular member 48 of the drip chamber assembly 42 is positioned slightly above the optical path of the emitters and detectors in the drip chamber yoke 37 so that the falling drops of fluid may be sensed by the emitters and detectors. As described above, the drip chamber shield 120 encloses the outer side of the top portion of the drip chamber assembly 42 to prevent ambient light from interfering with the operation of the emitters and detectors and to assist in retaining the tapered member of the drip chamber assembly 42 in the receiving recess 39 of the drip chamber yoke 37. The bottom end 53 of the drip chamber assembly 42 is positioned in the shoulder area 41 of the first mounting recess 68.

The silicone tube 44 is connected to the lower tubular member 52 of the drip chamber assembly 42 and extends downwardly from the first mounting recess 68 and through the first set loading tube channel 70 to contact one or more rollers 76 on the rotor 14. The silicone tube 44 is compressed around the rollers 76 so that a predetermined quantity of fluid is trapped between the spaced apart rollers 76. The silicone tube 44 also extends upwardly from the rotor 14 and passes rearwardly of the intermediate flange 126 on the rotor shield 122. The silicone tube 44 then extends through the silicone tube channel 115 to the second mounting recess 112. The stretching of the silicone tube 44 causes the mounting member 54 to seat in the shoulder area 111 in the second mounting recess 112 and behind the top flange 124 of the rotor shield 122 so that the magnet 62 on the annular flange 60 is positioned adjacent the sensor opening 114 in the swing arm 16. The positioning of the magnet 62 adjacent to the sensor opening 114 allows the magnetic sensor 117 in the housing assembly 12 to sense the presence of the magnet 62 and enable the operation of the motor 18 when the magnet 62 is sensed.

The outlet tube 64 of the fluid delivery set 40 extends upwardly through the receiving section 110 of the second set loading channel 90 and passes behind the retaining flange 38 on the housing assembly 12 and the ridges 98 on the swing arm 16. In prior peristaltic pumps, the outlet tube 64 would oftentimes be pinched at the connection of the outlet tube 64 and the top tubular member 56 of the mounting member 54 if the patient or the peristaltic pump were moved. This caused an increase in the back pressure in the silicone tube 44 so that the rollers 76 do not properly close or compress the silicone tube 44. In peristaltic pumps, the amount of fluid actually delivered to the patient through the fluid delivery set 40 by the peristaltic pump 10 decreases as the back pressure in the silicone tube 44 increases. Therefore, the outlet tube 64 in the present invention is designed to extend through the second set loading channel 90 as described above to prevent the outlet tube 64 from being pinched at the connection of the outlet tube 64 and the top tubular member 56 on the mounting member 54. Additionally, the sides of the second set loading channel 90 at the top surface 116 of the swing arm 16 are chamfered to decrease the likelihood that the flow of fluid will be impaired by pinching the outlet tube 64 against the swing arm 16.

Figure 16:
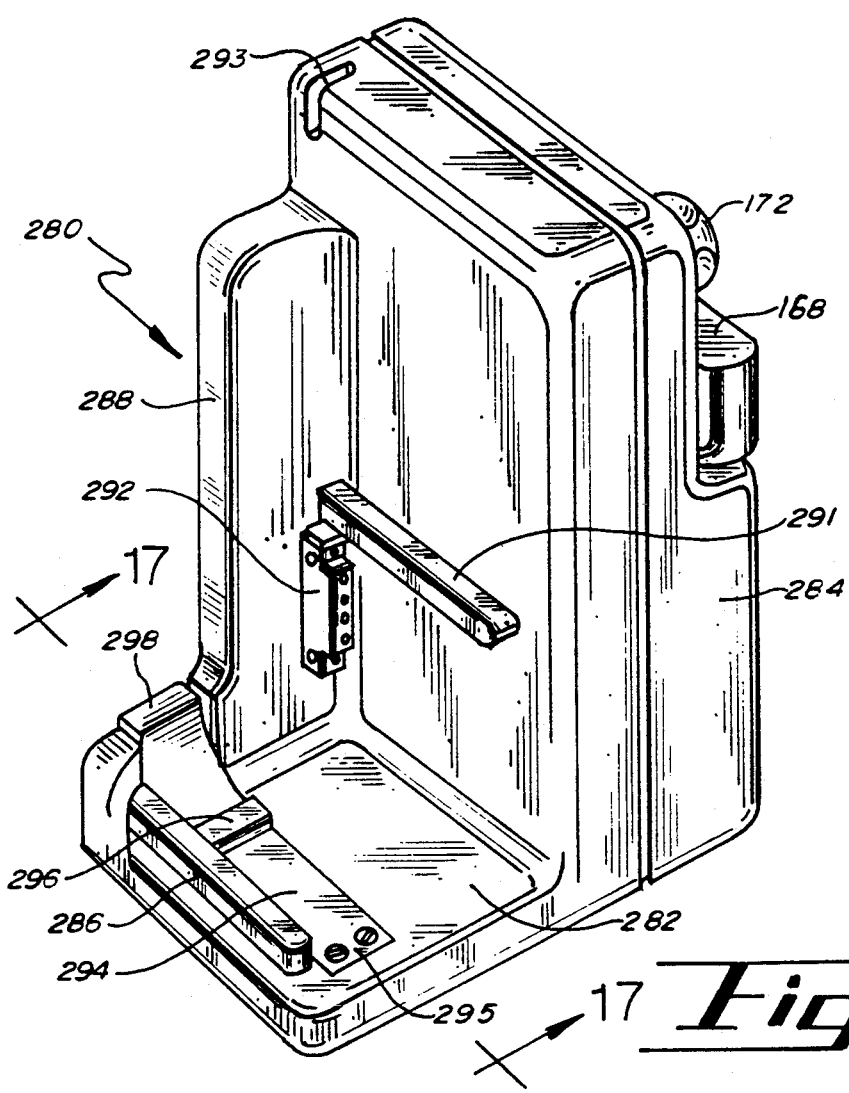
FIG. 16 is a frontal elevational view of an alternate embodiment of the charger unit of the present invention.

The present invention also includes a number of other features which are designed to prevent the swing arm from closing if the fluid delivery set 40 is improperly positioned in the housing assembly 12 and the swing arm 16. If the user inserts the mounting member 54 into the silicone tube channel 115 rather than in the receiving section 110, the rear end 128 of the intermediate flange 126 and the tapering section 113 of the second wall member channel 94 will push the circular mounting member 54 downwardly from the silicone tube channel 115 so that it will be visible along rear surface of the rotor and the magnet 62 will not be sensed by the magnetic sensor 177 to prevent the motor 18 from operating. If the user fails to properly place the outlet tube 64 behind the ridges 98 on the top of the swing arm 16, the outlet tube 64 will be pinched against the second wall member 94 of the swing arm 16 by the retaining flange 38 in the housing assembly 12 so that fluid flow will be restricted through the outlet tube 64. If the user places the silicone tube 44 in front of the rotor shield 122 rather than behind it, the silicone tube 44 will be pinched between the rear end 128 of the intermediate flange on the rotor shield 122 and the tapering section 113 on the second wall member 94 (FIG. 16). Finally, as described above, the receiving section 110 of the loading channel 90 is sized so that the user cannot inadvertently load the drip chamber assembly 42 in the receiving section 110 of the second set loading channel 90 because the drip chamber assembly 42 is too large to fit in the receiving section 110 of the second set loading channel 90.

As shown in FIGS. 11-15, the present invention also includes a charger unit 150 which is adapted to releasably receive the peristaltic pump 10 thereon. The charger unit 150 generally includes a base member 152 which is sized to slidably receive the bottom of the housing assembly 12 therein and an upwardly extending and generally rectangularly-shaped charger unit body member 154. As shown in FIG. 11, the base member 152 extends forwardly of the lower surface of the body member 154 and includes an upwardly extending forward lip 156 on the front surface thereof. A forwardly extending side lip 158 extends upwardly along the left side of the base member 152 and forwardly projects from the body member 154 to receive the front surface 20 of the housing assembly 12 therebehind. A latch opening 160 is located on the top surface of the base member 152 near the back of the base member 152 and adjacent to the side lip 158. Additionally, as shown in FIG. 14, a latch release opening 161 is located along the outer surface of the lower portion of the side lip 158.

The front surface of the body member 154 includes an elongate and generally rectangular slide member 162 which extends forwardly from the body member 154 a short distance below the approximate midpoint of the body member 154. As shown in FIG. 11, the slide member 154 extends horizontally from the intersection of the body member 154 and the side lip 158 to a rounded second end which is located near the opposite side of the body member 154. A conductive array of contact members 164 are oriented generally perpendicular to the slide member 162 and extend forwardly from the body member 154 along the intersection of the body member 154 and the side lip 158 below the slide member 162.

Figure 15:
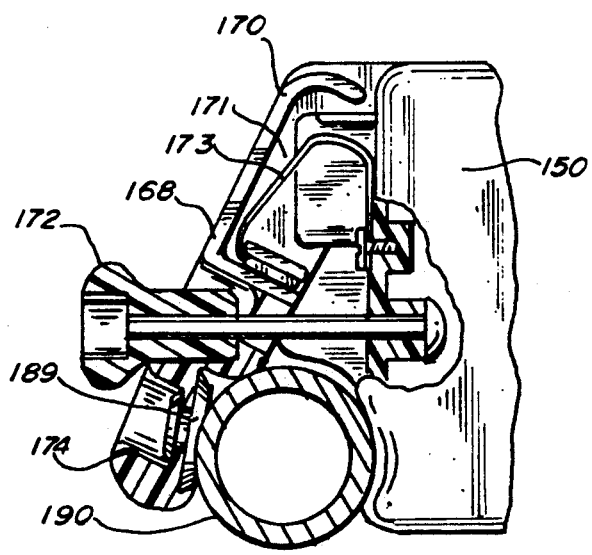
FIG. 15 is a partial cross-sectional view of the charger unit and pole clamp of the present invention.

As shown in FIG. 12, the rear surface of the body member 154 includes a lower semicircular support pole receiving surface 166 and a generally T-shaped pole clamp 168. The receiving surface 166 is positioned on the same side of the body member 154 as the side lip 158 and extends upwardly along the rear surface of the body member 154 approximately two-thirds of the distance along the member 154. The pole clamp 168 includes an elongate and horizontally oriented leg member 170 having a leaf spring retaining recess 171 therein; a threaded shaft member 172 extending therethrough and a vertically oriented clamping member 174 having a semi-circular recess on its interior surface. As shown in FIG. 15, the retaining recess 171 includes an outwardly biased leaf spring 173 which includes a first leg retained in the retaining recess 171 and a second leg which is biased against the rear surface of the charger unit 150.

As shown in FIG. 14, an elongate and semi-rigid latch member 176 is enclosed in a latch channel 178 located along the bottom surface of the base member 152. The latch member 176 is oriented generally parallel to the forward lip 156 and is positioned rearwardly thereof in the latch channel 178 located in the base member 152.

The right side of the latch member 176 includes a mounting surface 180 which is adapted to be fixedly mounted to the bottom surface of the base member 152 near the right side of the latch channel 178. A raised retaining member 182 extends upwardly from the latch member 176 to extend through the latch opening 16 on the top surface of the base member 152. In the present invention, the retaining member 182 includes a gradually upwardly sloping first surface which is nearest to the mounting surface 180 and a second surface which is oriented generally perpendicular to the bottom surface of the base member 152. A latch release member 183 extends upwardly from the left side of the latch member 176 to extend through the release opening 161 located on the outer surface of the side lip 158.

When the user desires to recharge the peristaltic pump 10; operate the peristaltic pump 10 with an external power source (not shown) or support the peristaltic pump 10 on a support pole 190, the peristaltic pump 10 is initially aligned with the right side of the charger unit 150 so that the elongate slide recess 184 (FIG. 6) on the rear surface of the housing assembly 12 is aligned with the slide member 162 on the forward surface of the body member 154. As the peristaltic pump 10 is moved to the left, the slide member 162 will align the contact members 164 on the charger unit 150 with contact members 186 (FIG. 6) on the rear side surface of the housing assembly 12 opposite the rotor 14. Once the peristaltic pump 10 reaches the side lip 158, the retaining member 182 on the latch member 176 will contact and enter the latch recess 188 (FIG. 6) on the bottom surface of the housing assembly 12 to releasably retain the peristaltic pump 10 on the charger unit 150. When the peristaltic pump 10 is retained in this position, the contact members 164 on the charger unit will be aligned with and in operative contact with the contact members 186 on the housing assembly 12 to allow the charger unit 150 to charge the batteries (not shown) and provide operating power to the peristaltic pump 10. When the batteries of the peristaltic pump 10 have been charged, the user may release the peristaltic pump 10 from the charger unit 150 by depressing the release member 183 on the outer surface of the side lip 158. When the release member 183 is depressed, the retaining member 182 is biased downwardly in the channel 178 so that the retaining member 182 is released from the latch recess 188 on the bottom surface of the housing assembly 12. The peristaltic pump 10 may then be moved to the right and removed from the charger unit 150.

Figure 13:
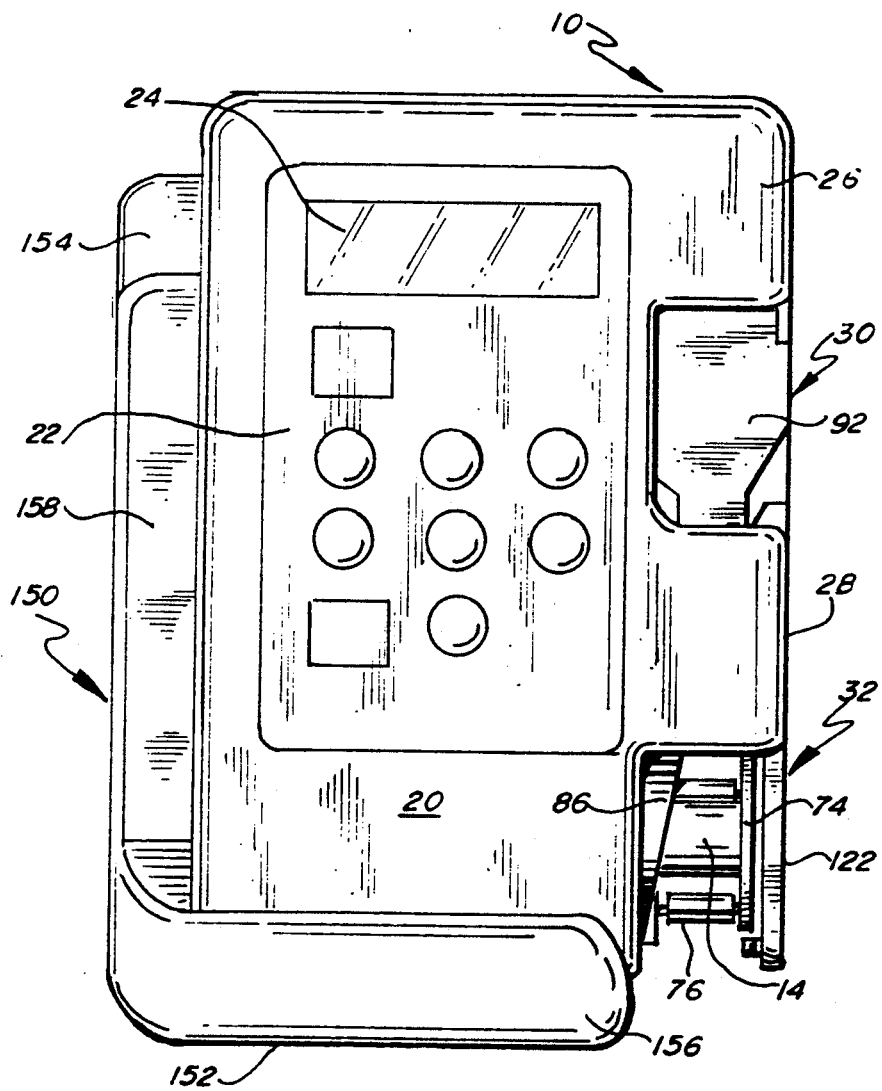
FIG. 13 is a frontal elevational view of the peristaltic pump mounted on the charger unit.

If the user desires to mount the peristaltic pump 10 to the support pole 190, the peristaltic pump 10 is initially inserted into the charger unit 150 as described above. The shaft member 172 on the pole clamp 168 is then unthreaded to allow the support pole to be inserted between the clamping member 174 and the rear surface of the body member 154 so that the support pole is aligned in the receiving surface 166 on the body member 154 and in compressive contact with a flexible pole receiving flange 189 on the inner surface of the clamping member 174. As shown in FIG. 15, the receiving flange 189 includes an interiorly directed flexible edge or bumper which is particularly designed to be compressed against the support pole 190 to frictionally retain the peristaltic pump 10 and charger unit 150 in position on the support pole 190. In this position, the leaf spring 173 pivotally biases the clamping member 174 outwardly from the rear surface of the body member 154 so that the right end of the leg member 170 pivotally maintains contact with the rear surface of the body member 154. As the connector 172 is threaded inwardly, the pole clamp 168 pivotally contacts the support pole 190 so that the receiving flange 189 of the clamping member 174 pivotally presses the support pole 190 against the rear surface of the body member 154 in the receiving surface 166 and the leg member 170 contacts the rear surface of the body member 154. As shown in FIG. 13, the swing arm 16 of the present invention is fully operational when the peristaltic pump 10 is mounted on the charger unit 150 and when the combination is mounted on a support pole 190.

Figure 17:
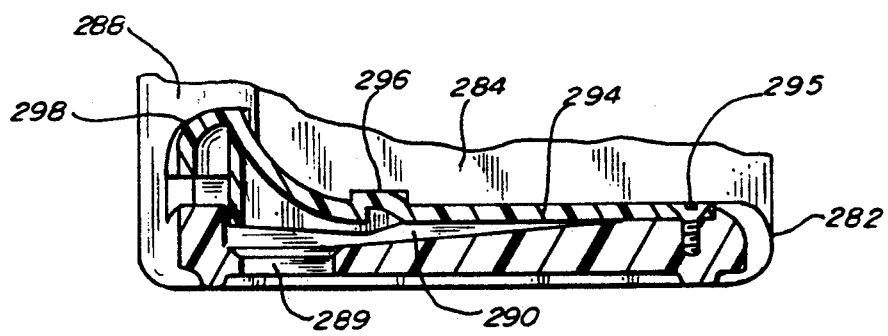
FIG. 17 is a partial cross-sectional view of the charger unit of FIG. 16 taken generally along lines 17—17 of FIG. 16.

FIGS. 16 and 17 illustrate an alternate form of the charger unit 280 which is adapted to releasably receive a peristaltic pump 10 mounted thereon for charging the pump or suspending the pump from an IV pole for bedside use. In describing the charger unit 280 of the present embodiment, reference is made to various surfaces and elements of the peristaltic pump 10 as described above. Like numbers have been added to like surfaces or elements of the above-described peristaltic pump 10 to assist in describing the present embodiment of the charger unit 280. The charger unit 280 generally includes a base member 282 which is sized to slidably receive the bottom of the housing assembly 12 thereon and an upwardly extending and generally rectangularly-shaped charger unit body member 284. As shown in FIG. 16, the base member 282 extends forwardly of the lower surface of the body member 284 and includes an upwardly extending and generally rectangularly-shaped forward lip 286 spaced inwardly from the front surface of the base member 282 and having a rounded second end thereon. The forward lip 286 of this embodiment is sized to be received in a similarly sized recess (not shown) on the bottom surface of a peristaltic pump (not shown) to retain the peristaltic pump on the charger unit 280 as described more fully hereinafter. A forwardly extending side lip 288 extends upwardly along the left side of the rear portion of the base member 282 and projects forwardly from the body member 284. The side lip 288 is designed to receive the left side of the housing assembly 12 adjacent thereto. A latch member receiving recess 290 is located on the base member 282 near the front of the base member 282 generally adjacent to and parallel with the forward lip 286 as shown in FIG. 16. A drainage opening 289 extends through the base member 282 in the receiving recess 290 to allow fluids which may be inadvertently spilled on the base member 282 of the charger unit 280 to drain from the receiving recess 290.

The front surface of the body member 284 includes an elongate and generally rectangular slide member 291 which extends forwardly from the body member 284 and is positioned a short distance below the approximate midpoint of the body member 284. As shown in FIG. 16, the slide member 291 extends horizontally from the intersection of the body member 284 and the side lip 288 to a rounded second end which is located near the opposite side of the body member 284. A conductive array of contact members such as a four pin contact member 292 is oriented generally perpendicular to the slide member 291 and forwardly from the body member 284 along the intersection of the body member 284 and the side lip 288. The contact member is positioned below the slide member 291 to provide an electrical contact between the charger unit 280 and the contact members 186 (FIG. 6) located along the left rear side of the peristaltic pump 10.

As shown in FIG. 16, the front surface of the body member 284 also includes a charging indictor 293 located generally above the side lip 288 and along the top surface of the charger unit 280. The charging indicator 293 of the present embodiment provides the user with a visually observable indication of when the charger unit 280 is connected to a power source and when the charger unit 280 is providing a charge to the peristaltic pump 10. When the charger unit 280 is connected to the power source or when the charger unit 280 is providing a steady or trickle charge to the batteries of the peristaltic pump 10, the charging indicator 293 is continuously illuminated. When the batteries of the peristaltic pump 10 are nearly run down, the charger unit 280 will provide a "quick charge" to the batteries for a certain period of time to increase to power of the batteries more rapidly than if a steady or trickle charge were applied to the batteries. When a quick charge is being applied to the batteries of the peristaltic pump 10, the charging indicator 293 will flash or flicker to signal the user that a quick charge is being applied to the batteries and that the batteries in the peristaltic pump 10 are low.

The elements and features on the rear surface of the body member 284 in the present embodiment are the same as the elements and features on the rear surface of the body member 154 as described above with respect to the preferred form of the charger unit 150. Therefore, the structure and function of the elements will not be separately discussed herein. As described previously and shown in FIG. 16, the rear surface of the body member 284 includes a T-shaped pole clamp 168 having a threaded shaft member 172 thereon.

As shown in FIG. 17, the latch member 294 is an elongate and semi-rigid member which is received in the latch receiving recess 290 located on the base member 282. The right side of the latch member 294 includes a mounting surface 295 which is adapted to be fixedly mounted to the bottom surface of the base member 282 near the right side of the recess 290. A raised retaining member 296 extends upwardly from the latch member 294 to extend upwardly from the generally flat top surface of the base member 282. In the present invention, the retaining member 296 includes a gradually upwardly sloping first surface which is nearest to the mounting surface 295 and a second surface which is oriented generally perpendicular to the bottom surface of the base member 282. A latch release member 298 extends upwardly from the left side of the latch member 294 to extend through the outer surface of the side lip 298. The portion of the latch member 294 between the retaining member 298 and the release member 298 is generally curved upwardly to conform to the rounded corner of the housing assembly 12 and to allow the latch member 294 to flex as the peristaltic pump 10 is mounted on the charger unit 280.

When the user desires to recharge the peristaltic pump 10; operate the peristaltic pump 10 with an external power source (not shown) or support the peristaltic pump 10 on a support pole as described above, the peristaltic pump 10 is initially aligned along the right side of the charger unit 280 so that the elongate slide recess 184 (FIG. 6) on the rear surface of the housing assembly 12 is aligned with the slide member 291 on the forward surface of the body member 254 and so that the forward lip 286 near the front of the base member 282 is aligned with the recess (not shown) on the bottom surface of the peristaltic pump. As the peristaltic pump 10 is moved to the left on the charger unit 280, the slide member 291 and forward lip 286 will align the contact member 292 on the charger unit 280 with contact members 186 (FIG. 6) on the rear side surface of the housing assembly 12 opposite the rotor 14. When the peristaltic pump 10 is mounted on the charger unit 280, the slide member 291 and forward lip 286 serve three functions: they aid in the proper alignment of the pump 10 with the charger unit 280, prevent the pump 10 from being removed in any direction other than from the right side of the charger unit 280 and cause a slight compressive fit to frictionally retain the pump 10 on the charger unit 280 against accidental detachment.

Once the peristaltic pump 10 reaches the side lip 288, the retaining member 296 on the latch member 294 will contact and enter the latch recess 188 (FIG. 6) on the bottom surface of the housing assembly 12 to releasably retain the peristaltic pump 10 on the charger unit 280. When the peristaltic pump 10 is retained in this position, the contact members 292 on the charger unit will be aligned with and in operative contact with the contact members 186 on the housing assembly 12 and the charging indicator 293 will be illuminated when the charger unit 280 is connected to a power source. This connection allows the charger unit 280 to charge the batteries (not shown) and provide the operating power necessary to operate the peristaltic pump 10. When the batteries of the peristaltic pump 10 have been charged, the user may release the peristaltic pump 10 from the charger unit 280 by depressing the release member 298 located along the top surface of the side lip 288. When the release member 298 is depressed, the retaining member 296 is flexed downwardly in the recess 290 so that the retaining member 296 is released from the latch recess 188 on the bottom surface of the housing assembly 12. The peristaltic pump 10 may then be moved to the right and removed from the charger unit 280.

If the user desires to mount the peristaltic pump 10 to a support pole, the peristaltic pump 10 is initially inserted into the charger unit 280 as described above and the pole clamp 168 is operated as described previously with the prior embodiment of the charger unit 150.

The preferred form of the present invention is described herein. It is anticipated that a number of modifications may be made to the present invention without departing from the intended scope of the present invention which is defined by the following claims.

What is claimed is:

1. A charger unit for use with a peristaltic pump, said charger unit comprising:
    a generally upright body member having front and rear surfaces, and an elongate slide member extending forwardly from said front surface;
    a forwardly extending base member extending forwardly from the lower portion of said body member, said base member being adapted to slidably receive at least a portion of the peristaltic pump thereon;
    a latch member movably mounted on said base member and adapted to releasably retain the peristaltic pump on said base member; and
    a clamp member on said body member to releasably receive a support pole longitudinally extending between said body member and an inner surface on said clamp member.

2. The charger unit of claim 1 further including a generally upright body member having front and rear surfaces extending upwardly from said base member, and said slide member extending forwardly from said front surface of said body member; and
    a forwardly extending side member extending forwardly from one side of said body member, said side member being adapted to slidably receive at least a portion of the peristaltic pump adjacent thereto.

3. The charger unit of claim 2 wherein said side member includes a contact member adjacent thereto to operatively receive a contact member from the peristaltic pump therein.

4. The charger unit of claim 3 wherein said body member includes a charging indicator thereon to visually indicate when said charger unit is charging the peristaltic pump.

5. The charger unit of claim 1 wherein said base member includes an upwardly extending lip member thereon adapted to be received in a recess on the peristaltic pump and wherein said lip member and said slide member cooperate to retain the peristaltic pump on said charger unit.

6. The charger unit of claim 1 wherein said clamp member includes
    a generally elongate first clamp section having a shaft member extending therethrough and a biased spring means operatively associated therewith;
    a second clamp section oriented generally perpendicular to said first clamp section and adapted to receive a support pole adjacent thereto; and
    said shaft member being movably received in said charger unit such that said first clamp section is generally parallel to said body member of said charger unit in a first closed position and said second clamp section is spaced apart from said charger unit by said spring means in a second open position wherein the support pole is insertable between said second clamp section and said charger unit.

7. The charger unit of claim 6 wherein said clamp member extends rearwardly from said rear surface of said body member and said rear surface of said body member includes a groove area thereon to receive a portion of the support pole therein.

8. A medical device comprising:
    a peristaltic pump for delivering medical fluid to a patient;
    a charger unit adapted to releasably receive said peristaltic pump thereon; and
    a clamp member operatively associated with said charger unit, said clamp member including a first clamp section having a shaft member extending therethrough and a biased spring means operatively associated therewith, a second clamp section oriented generally perpendicular to said first clamp section and adapted to receive a support pole adjacent thereto wherein said shaft member is movably received in said charger unit such that said first clamp section is generally parallel to said charger unit in a first closed position and said second clamp section is spaced apart from said charger unit by said spring means in a second open position wherein a support pole is insertable between said second clamp section and said charger unit.

9. The medical device of claim 8 wherein said charger unit further includes a generally upright body member having front and rear surfaces, a forwardly extending base member extending forwardly from the lower portion of said body member wherein said base member is adapted to slidably receive said peristaltic pump thereon and a latch member movably mounted on said charger unit and adapted to releasably retain said peristaltic pump on said charger unit.

10. The medical device of claim 9 wherein said clamp member extends rearwardly from said rear surface of said body member and said peristaltic pump is adapted to be received on said base member and adjacent to said front surface of said body member.

11. The medical device of claim 9 wherein said latch member is mounted on said base member and includes a first section thereon to engage a portion of said peristaltic pump to retain said peristaltic pump on said charger unit and a second section which is adapted to be depressed to release said first section from said portion of said peristaltic pump.

12. The medical device of claim 9 wherein said charger unit includes a side lip extending forwardly from said body member and said peristaltic pump is adapted to be received adjacent said side lip and said body member when said peristaltic pump is mounted on said charger unit.

13. The medical device of claim 12 wherein said side lip includes a first contact member adjacent thereto and said peristaltic pump includes a similarly oriented second contact member thereon such that said first and second contact members operatively engage each other when said peristaltic pump is properly mounted on said charger unit.

14. The medical device of claim 8 wherein said charger unit includes a first slide member extending forwardly from a first surface thereon and a second slide member extending upwardly from a second surface thereon and wherein said first and second slide members are adapted to be received in first and second recesses on said peristaltic pump to releasably retain said peristaltic pump on said charger unit.

15. The medical device of claim 14 wherein said charger unit includes an indicating means thereon to indicate when said charger unit is charging said peristaltic pump.

16. A medical device comprising:
a peristaltic pump having a first recess thereon;
a charger unit adapted to releasably receive said peristaltic pump therein, said charger unit including a generally upright body member having front and rear surfaces, and an elongate slide member extending forwardly from said front surface and adapted to be received in said first recess on said peristaltic pump and a forwardly extending base member extending forwardly from the lower portion of said body member, said base member being adapted to slidably receive at least a portion of said peristaltic pump thereon;
a latch member operatively mounted on said charger unit and adapted to releasably retain said peristaltic pump on said charger unit; and
a side lip on said charger unit extending forwardly from one side of said body member wherein said side lip and said front surface of said body member are adapted to receive said peristaltic pump operatively associated therewith.

17. The medical device of claim 16 wherein a clamp member extends rearwardly from said rear surface of said body member and further includes a first clamp section having a shaft member operatively extending therethrough and a biased spring means operatively associated therewith, and a second clamp section of said clamp member is oriented generally perpendicular to said first clamp section and is adapted to receive a support pole adjacent thereto, said shaft member being movably received in said charger unit such that said first clamp section is generally parallel to said charger unit in a first closed position and said second clamp section is spaced apart from said charger unit by said spring means in a second open position wherein the support pole is insertable between said second clamp section and said charger unit.

18. A medical device for supporting a peristaltic pump on a support pole, said device comprising:
a support member adapted to releasably receive and support a peristaltic pump thereon, said support member including a generally upright body member having front and rear surfaces, and an elongate slide member extending forwardly from said front surface and adapted to be received in a recess on the peristaltic pump and a forwardly extending base member extending forwardly from the lower portion of said body member, said base member being adapted to slidably receive at least a portion of said peristaltic pump thereon;
a latch member operatively mounted on said support member and adapted to releasably retain the peristaltic pump on said support member;
a side lip on said support member extending forwardly from one side of said body member wherein said side lip and said front surface of said body member are adapted to receive the peristaltic pump operatively associated therewith; and
a clamp member on said support member for removably mounting said support member on a support pole.

19. The medical device of claim 18 wherein said clamp member extends rearwardly from said rear surface of said body member and further includes a first clamp section having a shaft member operatively extending therethrough and a biased spring means operatively associated therewith, and a second clamp section of said clamp member is oriented generally perpendicular to said first clamp section and is adapted to receive a support pole adjacent thereto, said shaft member being movably received in said support member such that said first clamp section is generally parallel to said support member in a first closed position and said second clamp section is spaced apart from said support member by said spring means in a second open position wherein the support pole is insertable between said second clamp section and said support member.

20. The medical device of claim 18 further including means for providing an electrical contact between said support member and the peristaltic pump wherein said providing means is operatively associated with said support member.

* * * * *